United States Patent [19]

Pelosi, Jr. et al.

[11] 4,078,141

[45] Mar. 7, 1978

[54] 5-(2-NITROPHENYL)-2-FURANCARBOXIMIDOYL MORPHOLINE OR PYRROLIDINE HYDROCHLORIDE

[75] Inventors: Stanford S. Pelosi, Jr.; Ronald E. White; George C. Wright; Chia Nien Yu, all of Norwich, N.Y.

[73] Assignee: Morton-Norwich Products, Inc., Norwich, N.Y.

[21] Appl. No.: 765,622

[22] Filed: Jan. 25, 1977

[51] Int. Cl.$^2$ .................. C07D 405/02; C07D 413/02
[52] U.S. Cl. ............................. 544/152; 424/248.57; 424/285; 260/326.5 D
[58] Field of Search ................. 260/247.5 H, 326.5 D

[56] References Cited

PUBLICATIONS

Descamps et al., "Chem Abstracts" vol. 80 (1974), No. 96017m.
Pelosi et al., "Chem Abstracts" vol. 84 (1976), No. 30857m.

*Primary Examiner*—Henry R. Jiles
*Assistant Examiner*—R. W. Ramsuer
*Attorney, Agent, or Firm*—Anthony J. Franze

[57] ABSTRACT

5-(2-Nitrophenyl)-2-furancarboximidoyl morpholine or pyrrolidine hydrochloride are useful as antidepressants.

3 Claims, No Drawings

5-(2-NITROPHENYL)-2-FURANCARBOXIMIDOYL MORPHOLINE OR PYRROLIDINE HYDROCHLORIDE

This invention is concerned with 5-(2-nitrophenyl)-2-furancarboximidoyl morpholine or pyrrolidine hydrochloride of the formula:

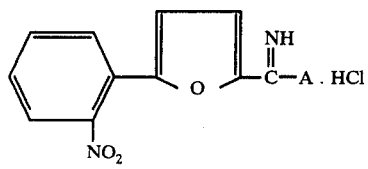

wherein A represents 4-morpholinyl or 1-pyrrolidinyl.

These compounds are useful as antidepressants. Their useful antidepressant activity is exhibited in warm blooded animals under the standard ptosis-antitetrabenazine test. Thus, when administered perorally in suspension or aqueous solution in a dose of 50 mg/kg to mice shortly prior to intraperitoneal administration of from 1-10 mg/kg of tetrabenazine, ptosis induced by tetrabenazine is curtailed to the extent of from 70-80%.

The compounds of this invention are currently preferably prepared according to the following scheme:

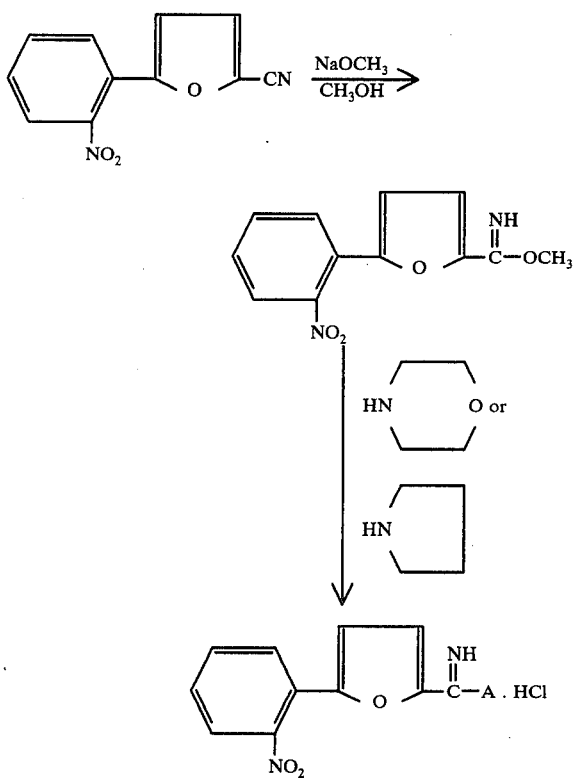

wherein A represents 4-morpholinyl or 1-pyrrolidinyl. The following examples illustrate the method of preparation.

EXAMPLE I

4-[5-(2-Nitrophenyl)-2-furancarboximidoyl]morpholine Hydrochloride

A mixture of 5-(2-nitrophenyl)-2-furonitrile (92 g, 0.43 mole) and anhydrous methanol (1000 ml) was heated to 55° and sodim methoxide (1.5 g) was added. The steam bath was removed, the solution was stirred for two hours and stored overnight at room temperature. The solution was poured into ice water (1000 ml) and stirred for one hour. The solid was collected by filtration and air dried to yield 91 g (86%) of methyl 5-(2-nitrophenyl)-2-furancarboximidamide. A sample was recrystallized from isopropanol, m.p. 107°-108°.

Anal. Calcd. for $C_{12}H_{10}N_2O_4$: C, 58.54; H, 4.09; N, 11.38 Found: C, 58.56; H, 3.87; N, 11.26.

A mixture of the above compound (29 g, 0.12 mole), ethanol (300 ml), and morpholine (10.4 g, 0.12 mole) was stirred for 15 hours at room temperature and refluxed for 8 hours. The mixture was stripped of solvent under reduced pressure, the product was extracted with hot cyclohexane, Darco added, and filtered. The filtrate was reduced in volume to 200 ml under reduced pressure, cooled, and the cyclohexane was decanted. The product was dissolved in isopropanol, the solution was adjusted to pH 2 with isopropanol/HCl and stored overnight at room temperature. The product was collected by filtration, yield: 19 g (47%). A sample was recrystallized from ethanol, m.p. 231°-235°.

Anal. Calcd, for $C_{15}H_{15}N_3O_4 \cdot HCl$: C, 53.34; H, 4.77; N, 12.44. Found: C, 53.41; H, 5.01; N, 12.20.

EXAMPLE II

1-[5-(2-Nitrophenyl)-2-furancarboximidoyl]pyrrolidine Hydrochloride

A mixture of methyl 5-(2-nitrophenyl)-2-furancarboximidamide (18 g, 0.075 mole), ethanol (175 ml), and pyrrolidine (5.4 g, 0.075 mole) was refluxed for 7 hours and stored overnight at room temperature. The mixture was stripped of solvent under reduced pressure, isopropanol was added, and the mixture was again stripped of solvent. The residue was dissolved in cyclohexane (600 ml), Darco added, filtered, and the filtrate cooled. The crystallized material was collected by filtration. This material was dissolved in isopropanol, and isopropanol/HCl was added to adjust the solution to pH 2. The solution was cooled and the product was collected by filtration. The product was recrystallized from isopropanol; m.p. 236°-238°, yield: 20 g (83%).

Anal. Calcd. for $C_{15}H_{15}N_3O_3 \cdot HCl$: C, 55.95; H, 5.01; N, 13.06. Found: C, 55.87; H, 4.96; N, 13.40.

What is claimed is:

1. A compound of the formula:

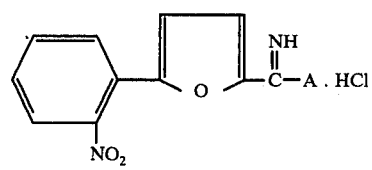

wherein A represents 4-morpholinyl or 1-pyrrolidinyl.

2. The compound 4-[5-(2-nitrophenyl)-2-furancarboximidoyl]-morpholine hydrochloride.

3. The compound 1-[5-(2-nitrophenyl)-2-furancarboximidoyl]-pyrrolidine hydrochloride.

* * * * *